(12) United States Patent
DeLuca et al.

(10) Patent No.: US 9,416,102 B2
(45) Date of Patent: Aug. 16, 2016

(54) (22E)-2-METHYLENE-22-DEHYDRO-1α,24,25-TRIHYDROXY-19-NOR-VITAMIN D₃ ANALOGS

(71) Applicant: Wisconsin Alumni Research Foundation, Madison, WI (US)

(72) Inventors: Hector F. DeLuca, Deerfield, WI (US); Lori A. Plum, Arena, WI (US); Rafal Barycki, Madison, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/084,281

(22) Filed: Nov. 19, 2013

(65) Prior Publication Data

US 2014/0206655 A1    Jul. 24, 2014

Related U.S. Application Data (60) Provisional application No. 61/755,702, filed on Jan. 23, 2013.

(51) Int. Cl.
| | | |
|---|---|---|
| *A61K 31/593* | (2006.01) | |
| *C07C 401/00* | (2006.01) | |
| *A61K 31/592* | (2006.01) | |

(52) U.S. Cl.
CPC ............. *C07C 401/00* (2013.01); *A61K 31/592* (2013.01); *A61K 31/593* (2013.01); *C07C 2101/14* (2013.01); *C07C 2102/24* (2013.01)

(58) Field of Classification Search
CPC ............................. C07C 401/00; A61K 31/593
USPC ............................................. 552/653; 514/167
See application file for complete search history.

(56) References Cited

U.S. PATENT DOCUMENTS

| | | | |
|---|---|---|---|
| 5,086,191 | A | 2/1992 | DeLuca et al. |
| 5,536,713 | A | 7/1996 | DeLuca et al. |
| 5,545,633 | A | 8/1996 | Bretting |
| 5,843,928 | A | 12/1998 | DeLuca et al. |
| 5,929,056 | A | 7/1999 | Mourino et al. |
| 5,945,410 | A | 8/1999 | DeLuca et al. |
| 6,399,797 | B1 | 6/2002 | von Daehne et al. |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |

FOREIGN PATENT DOCUMENTS

| | | |
|---|---|---|
| WO | 2005018658 A1 | 3/2005 |
| WO | 2005051323 A2 | 6/2005 |
| WO | 2008083370 A2 | 7/2008 |

OTHER PUBLICATIONS

Arbour et al., "A Highly Sensitive Method for Large-Scale Measurements of 1,25-Dihydroxyvitamin D", Analytical Biochemistry, 1998, 255: 148-154.
Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.
Collins et al., "Normal Functional Characteristics of Cultured Human Promyelocytioc Leukemia Cells (HL-60) After Induction of Differentiation by Dimethylsulfoxide", The Journal of Experimental Medicine, 1979, 149: 969-974.
Lythgoe et al., "Calciferol and its Relatives. Part 22. A Direct Total Synthesis of Vitamin D2 and Vitamin D3", J. Chem. Soc. Perkin I, 1978, 590-595.
Lythgoe, "Synthetic Approaches to Vitamin D and its Relatives", Chem. Soc. Rev., 1983, 9: 449-475.
Osterm et al., "24- and 26-homo-1,25-dihydroxyvitamin D3: Preferential Activity in Inducing Differentiation of Human Leukemia Cells HL-60 in vitro", Proc. Natl. Acad. Sci. USA, 1987, 84: 2610-2614.
Perlman et al., "1alpha,25-dihydroxyvitamin D3, A Novel Vitamin D-related Compound with Potential Therapeutic Activity", Tetrahedron Letters, 1990, 31: 1823-1824.
Perlman et al., "Novel Synthesis of 19-Nor-Vitamin D Compounds", Tetrahedron Letters, 1991, 32: 7663-7666.
Sardina et al., "Studies on the Synthesis of Side-Chain Hydroxylated Metabolites of Vitamin D. 2. Stereocontrolled Synthesis of 25-Hydroxyvitamin D2", Journal of Organic Chemistry, 1986, 51: 1264-1269.
Toh et al., "Studies on a Convergent Route to Side-Chain Analogues of Vitamin D:25-Hydroxy-23-oxavitamin D3", Journal of Organic Chemistry, 1983, 48: 1414-1417.
Plum et al., "Vitamin D, Disease and Therapeutic Opportunities", Nature Reviews Drug Discovery, 2010, 9(12): 941-955.
Sakamaki et al., "Potent Antagonist for the Vitamin D Receptor: Vitamin D Analogues with Simple Side Chain Structure", Journal of Medicinal Chemistry, American Chemical Society, 2010, 53(15): 5813-5826.
International Search Report and Written Opinion, PCT International Application No. PCT/US2013/077486, mailed May 9, 2014.
International Preliminary Report on Patentability mailed Jul. 28, 2015 for PCT/US2013/077486.

*Primary Examiner* — Barbara P Badio
(74) *Attorney, Agent, or Firm* — Andrus Intellectual Property Law, LLP (57) ABSTRACT

Disclosed are (22E)-2-methylene-22-dehydro-1,24,25-trihydroxy-19-nor-vitamin D₃ compounds, their biological activities, and various pharmaceutical uses for these compounds. Particularly disclosed are (22E)-(24R)-2-methylene-22-dehydro-1α,24,25-trihydroxy-19-nor-vitamin D₃ and (22E)-(24S)-2-methylene-22-dehydro-1α,24,25-trihydroxy-19-nor-vitamin D₃, their biological activities, and various pharmaceutical uses for these compounds.

18 Claims, 7 Drawing Sheets

(22E)-2-METHYLENE-22-DEHYDRO-1α,24,25-TRIHYDROXY-19-NOR-VITAMIN $D_3$ ANALOGS

CROSS REFERENCE TO RELATED APPLICATIONS

This application claims the benefit under 35 U.S.C. §119 (e) to U.S. Provisional Application No. 61/755,702, filed on Jan. 23, 2013, which is incorporated by reference herein in its entirety.

BACKGROUND

The field of the invention relates to vitamin D compounds, and more particularly to (22E)-2-methylene-22-dehydro-1α,24,25-trihydroxy-19-nor-vitamin $D_3$ analogs and their pharmaceutical uses.

The natural hormone, 1α,25-dihydroxyvitamin $D_3$ and its analog in the ergosterol series, i.e., 1α,25-dihydroxyvitamin $D_2$, are known to be highly potent regulators of calcium homeostasis in animals and humans, and their activity in cellular differentiation has also been established. (See Ostrem et al., Proc. Natl. Acad. Sci. USA, 84, 2610 (1987)). Many structural analogs of these metabolites have been prepared and tested, including 1α-hydroxyvitamin $D_3$, 1α-hydroxyvitamin $D_2$, various side-chain homologated analogs, and fluorinated analogs. Some of these vitamin D analogs exhibit biological activities that differ from the biological activities of the native vitamin D compounds, including decreased or increased biological activity related to calcium regulation and cell differentiation as compared to the native vitamin D compounds. The difference in biological activities exhibited by vitamin D analogs may be exploited in the treatment of a variety of diseases such as renal osteodystrophy, vitamin D-resistant rickets, osteoporosis, psoriasis, and certain malignancies, where some of the biological activities of vitamin D compounds are desirable, but other of the biological activities of vitamin D compounds are not desirable.

One class of vitamin D analogs, i.e., the so called 19-nor-vitamin D compounds, is characterized by the replacement of the A-ring exocyclic methylene group (carbon 19), typical of the vitamin D system, by two hydrogen atoms. Several 19-nor-analogs (e.g., 1α,25-dihydroxy-19-nor-vitamin $D_3$) exhibit a selective, biological activity profile characterized by a high potency in inducing cellular differentiation, and a low potency in inducing calcium-mobilizing activity. Thus, some of these compounds are potentially useful as therapeutic agents for the treatment of malignancies or the treatment of various skin disorders. Methods for synthesizing such 19-nor-vitamin D analogs have been described. (See Perlman et al., Tetrahedron Lett. 31, 1823 (1990); Perlman et al., Tetrahedron Lett. 32, 7663 (1991), and DeLuca et al., U.S. Pat. No. 5,086,191).

Vitamin $D_3$ analogs substituted at carbon 2 (C-2) also have been synthesized, including compounds substituted at C-2 with: hydroxy or alkoxy groups (DeLuca et al., U.S. Pat. No. 5,536,713); 2-alkyl groups (DeLuca et al., U.S. Pat. No. 5,945,410); and 2-alkylidene groups (DeLuca et al., U.S. Pat. No. 5,843,928). Like the 19-nor analogs, these compounds also exhibit selective, biological activity profiles. In particular, U.S. Pat. No. 5,843,928 discloses a 2-methylene-(20S)-1α,25-dihydroxy-19-nor-vitamin $D_3$ analog otherwise referred to as "2MD." Studies of these analogs indicate that binding sites in vitamin D receptors can accommodate different substituents at C-2 in the synthesized vitamin D analogs.

Additional vitamin D analogs have been synthesized and tested, including analogs which are characterized by the presence of a methylene substituent at carbon 2 (C-2), a hydroxyl group at both carbon 1 (C-1) and carbon 3 (C-3), and a shortened side chain attached to carbon 20 (C-20). (See DeLuca et al., U.S. Pat. No. 6,566,352, disclosing 1α-hydroxy-2-methylene-19-nor-pregnacalciferol; DeLuca et al., U.S. Pat. No. 6,579,861, disclosing 1α-hydroxy-2-methylene-19-nor-homopregnacalciferol; and DeLuca et al., U.S. Pat. No. 6,627,622, disclosing 1α-hydroxy-2-methylene-19-nor-bishomopregnacalciferol). These analogs exhibit a relatively high binding activity to vitamin D receptors and a relatively high cell differentiation activity, but little if any calcemic activity as compared to 1α,25-dihydroxyvitamin $D_3$. The biological activities of these analogs make them excellent candidates for a variety of pharmaceutical uses.

Vitamin D analogs having 17-ene double bonds as well as vitamin D compounds having a double bond in the side chain also are known and have been proposed for various pharmacological uses. (See Bretting, U.S. Pat. No. 5,545,633; Mourino et al., U.S. Pat. No. 5,929,056; and von Daehne, et al., U.S. Pat. No. 6,399,797). Bone diseases such as osteoporosis, skin disorders such as psoriasis, cancers such as leukemia, and cosmetic conditions such as wrinkles are just some of the applications proposed for such compounds. 2-alkylidene compounds having a side chain with a double bond therein also have been described (See DeLuca et al., U.S. Pat. No. 5,843,928).

Although a large number of vitamin D analogs exist, new analogs that may be utilized in therapeutic methods are desirable. Here, the inventors describe further vitamin D analogs.

SUMMARY

Disclosed are (22E)-2-methylene-22-dehydro-1α,24,25-trihydroxy-19-nor-vitamin $D_3$ compounds, their biological activities, and various pharmaceutical uses for these compounds. These new vitamin D compounds are 19-nor-vitamin D analogs having a methylene group at the carbon 2 position (C-2), a desaturated carbon at the carbon 22 position (C-22) resulting in a double bond between carbon 22 and carbon 23 (C-23), and hydroxyl groups at carbon 1 (C-1), carbon 24 (C-24), and carbon 25 (C-25). These compounds may also be named, and may be referred to herein, especially in the description of their synthesis herein and the schemes, as (22E)-2-methylene-22-dehydro-1α,24,25-trihydroxy-19-nor-vitamin $D_3$ analogs. The preferred vitamin $D_3$ analogs are (22E)-(24R)-2-methylene-22-dehydro-1α,24,25-trihydroxy-19-nor-vitamin $D_3$, otherwise referred to herein as "WT-51," and (22E)-(24S)-2-methylene-22-dehydro-1α,24,25-trihydroxy-19-nor-vitamin $D_3$, otherwise referred to herein as "WT-52."

Structurally these (22E)-2-methylene-22-dehydro-1α,24,25-trihydroxy-19-nor-vitamin $D_3$ analogs are characterized by the general formula I shown below:

I where $X_1$, $X_2$, $X_3$, and $X_4$, which may be the same or different, are each selected from hydrogen or a hydroxy-protecting group.

One preferred analog is (22E)-(24R)-2-methylene-22-dehydro-1α,24,25-trihydroxy-19-nor-vitamin $D_3$, otherwise referred to herein as "WT-51," which has the following formula Ia:

Ia

Another preferred analog is (22E)-(24S)-2-methylene-22-dehydroxy-1α,24,25-trihydroxy-19-nor-vitamin $D_3$, otherwise referred to herein as "WT-52," which has the following formula Ib:

Ib

As described herein, these compounds exhibit a desired, and highly advantageous pattern of biological activity. The compounds may be utilized in methods for treating and/or preventing diseases or disorders associated with vitamin D activity in a patient in need thereof. In some embodiments, the compounds disclosed herein may be utilized in methods for treating and/or preventing bone diseases and disorders, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. The disclosed compounds also may be administered in methods for increasing bone strength in a patient.

In other embodiments, the compounds disclosed herein may be utilized in methods for treating and/or preventing skin diseases, disorders, and conditions in a patient in need thereof. These may include, but are not limited to psoriasis, acne, lack of adequate skin firmness, lack of adequate dermal hydration, and insufficient sebum secretion.

In further embodiments, the compounds disclosed herein may be utilized in methods for treating and/or preventing cell proliferative diseases or disorders such as cancer in a patient in need thereof. These may include, but are not limited to leukemia, colon cancer, breast cancer, skin cancer, and prostate cancer.

In even further embodiments, the compounds disclosed herein may be utilized in methods for treating and/or preventing autoimmune diseases and disorders in a patient in need thereof. These may include, but are not limited to multiple sclerosis, diabetes mellitus, lupus, host versus graft reaction, and rejection of transplants.

In even further embodiments, the compounds disclosed herein may be utilized in methods for treating and/or preventing inflammatory diseases. These may include, but are not limited to rheumatoid arthritis, asthmas, and inflammatory bowel diseases. The compounds may be utilized specifically in methods of treating or preventing inflammatory bowel diseases that include Crohn's disease and ulcerative colitis.

In even further embodiments, the compounds disclosed herein may be utilized in methods for treating and/or preventing obesity, inhibiting adipocyte differentiation, inhibiting SCD-1 gene transcription, and/or reducing body fat.

In even further embodiments, the compounds disclosed herein may be utilized in methods for treating and/or preventing secondary hyperparathyroidism, for example, secondary hyperparathryoidism of renal osteodystrophy.

DETAILED DESCRIPTION

The disclosed subject matter further may be described utilizing terms as defined below.

Unless otherwise specified or indicated by context, the terms "a", "an", and "the" mean "one or more." For example, the phrases "a compound" and "an analog" should be interpreted to mean "one or more compounds" and "one or more analogs," respectively.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The transitional term "comprising" should be interpreted as being "open-ended" such that a claim utilizing the term "comprising" should be interpreted as requiring the recited components but being permitted to include other additional components. The transitional term "consisting essentially of" should be interpreted as being "partially closed" such that a claim utilizing the term "consisting essentially of" should be interpreted as requiring the recited components and permitting only other additional components that do not materially affect the basic and novel characteristics of the claimed subject matter. The transitional term "consisting" should be interpreted as being "closed" such that a claim utilizing the term "consisting" should be interpreted as requiring the recited components and permitting no other additional components.

As used herein, the terms "native hormone" and "1α,25 (OH)$_2$D$_3$" may be used interchangeably.

As used herein, the compound "WT-51" refers to (22E)-(24R)-2-methylene-22-dehydro-1α,24,25-trihydroxy-19-nor-vitamin D$_3$.

As used herein, the compound "WT-52" refers to (22E)-(24S)-2-methylene-22-dehydro-1α,24,25-trihydroxy-19-nor-vitamin D$_3$.

As used herein, the compound "2MD" refers to 2-methylene-(20S)-1α,25-dihydroxy-19-nor vitamin D$_3$. (See DeLuca et al., U.S. Pat. No. 5,843,928).

The presently disclosed analogs are characterized by the general formula I previously illustrated herein. The pro-drug form and protected-hydroxy form of the presently disclosed analogs also are characterized by general formula I. As contemplated herein, a "protected hydroxy" group is a hydroxy group derivatized or protected by any of the above groups commonly used for the temporary or permanent protection of hydroxy functions (e.g., a silyl, alkoxyalkyl, acyl or alkoxycarbonyl groups, as described herein). A "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. As contemplated herein, the word "alkyl" as used in the description or the claims, denotes a straight-chain or branched alkyl radical of 1 to 10 carbons, in all its isomeric forms. "Alkoxy" refers to any alkyl radical which is attached by oxygen (i.e., a group represented by "alkyl-O—"). Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. The terms "hydroxyalkyl", "deuteroalkyl" and "fluoroalkyl" refer to an alkyl radical substituted by one or more hydroxy, deuterium, or fluoro groups respectively. An "alkylidene" refers to a radical having the general formula $C_kH_{2k}$—where K is an integer.

The preparation of (22E)-2-methylene-22-dehydro-1α,24,25-trihydroxy-19-nor-vitamin D$_3$ analogs having the structure 1 may be accomplished by a common general method, for example, as illustrated in Schemes I and II. Scheme I illustrates a method for preparing precursor ketone 7 which is then condensed with the allylic phosphine oxide 8 to the corresponding 2-methylene-22-dehydro-1α,24,25-trihydroxy-19-nor-vitamin D$_3$ analog 9, which includes protected-hydroxy groups at carbon 1 (C-1), carbon 3 (C-3), carbon 24 (C-24) and carbon 25 (C-25). The (22E)-2-methylene-22-dehydro-1α,24,25-trihydroxy-19-nor-vitamin D$_3$ analog 9 subsequently is deprotected at carbon 1 (C-1), carbon 3 (C-3), carbon 24 (C-24) and carbon 25 (C-25) to yield the (22E)-(24R)-2-methylene-22-dehydro-1α,24,25-trihydroxy-19-nor-vitamin D$_3$ analog 10 and the (22E)-(24S)-2-methylene-22-dehydro-1α,24,25-trihydroxy-19-nor-vitamin D$_3$ analog 11.

In Scheme I, protection of the hydroxy groups is provided by one of a benzoyl group (Bz), a triethyl silyl group (TES), and t-butyldimethylsilyl group (TBS). Although Bz, TES, and TBS groups are utilized in Scheme I as hydroxy-protecting groups, any hydroxy-protecting group, as described herein, may be utilized during the reaction steps. In Scheme I, precursor 3 is prepared by reacting substrate 1 and substrate 2, which may be prepared by the method shown in Scheme II herein.

The condensation step in Scheme I forming analog 9 represents an application of the convergent synthesis concept, which has been applied effectively for the preparation of vitamin D compounds. (See Lythgoe et al., J. Chem. Soc. Perkin Trans. I, 590 (1978); Lythgoe. Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; and DeLuca et al., U.S. Pat. No. 5,536,713).

For the preparation of the required phosphine oxides of general structure 8, a synthetic route has been developed starting from a methyl quinicate derivative which is easily obtained from commercial (1R,3R,4S,5R)-(−)-quinic acid. (See Perlman et al., Tetrahedron Lett. 32, 7663 (1991); and DeLuca et al., U.S. Pat. No. 5,086,191).

As disclosed herein, the (22E)-2-methylene-22-dehydro-1α,24,25-trihydroxy-19-nor-vitamin D$_3$ analogs may be utilized to treat and/or prevent diseases or disorders in patients in need thereof. The terms "patient," "subject," and "individual" may be used interchangeably herein.

A patient in need thereof may include any animal. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

A patient in need thereof may refer to patient having or at risk for acquiring a disease or disorders associated with vitamin D activity. For example, a patient in need thereof may include a patient having or at risk for acquiring bone diseases and disorders, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. A patient in need thereof may also include a patient in need of an increase in bone strength.

A patient in need thereof may include a patient having or at risk for developing skin diseases, disorders, and conditions. These may include, but are not limited to psoriasis, acne, lack of adequate skin firmness, lack of adequate dermal hydration, and insufficient sebum secretion.

A patient in need thereof may include a patient having or at risk for developing cell proliferative diseases or disorders such as cancer. These may include, but are not limited to leukemia, colon cancer, breast cancer, skin cancer, and prostate cancer.

A patient in need thereof may include a patient having or at risk for developing autoimmune diseases and disorders. These may include, but are not limited to multiple sclerosis, diabetes mellitus, lupus, host versus graft reaction, and rejection of transplants.

A patient in need thereof may include a patient having or at risk for developing an inflammatory disease or disorder. These may include, but are not limited to rheumatoid arthritis, asthmas, and inflammatory bowel diseases. A patient in need thereof may include having or at risk for developing Crohn's disease and ulcerative colitis.

A patient in need thereof may include a patient having or at risk for developing obesity. A patient in need thereof may include a patient in need of or desirous of inhibiting adipocyte differentiation, inhibiting SCD-1 gene transcription, and/or reducing body fat.

A patient in need thereof may include a patient having or at risk for developing secondary hyperparathyroidism. In particular, a patient in need thereof may include a patient having or at risk for developing secondary hyperparathyroidism of renal osteodystrophy.

For prevention and/or treatment purposes, the compounds of this invention defined by formula I, particularly WT-51 and WT-52, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, antioxidants, binders, coloring agents or emulsifying or taste-modifying agents.

The compounds of formula I, particularly WT-51 and WT-52, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications.

A dose of from 0.01 µg to 1000 µg per day of the compounds I, particularly WT-51 and WT-52, preferably from about 0.1 µg to about 500 µg per day, is appropriate for prevention and/or treatment purposes, such dose being adjusted according to the disease to be treated, its severity and the response of the subject as is well understood in the art. Because the compound exhibits specificity of action, each may be suitably administered alone, or together with graded doses of another active vitamin D compound (e.g., 1α-hydroxyvitamin $D_2$ or $D_3$, or 1α,25-dihydroxyvitamin $D_3$) in situations where different degrees of bone mineral mobilization and calcium transport stimulation is found to be advantageous.

Compositions for use in the above-mentioned treatments comprise an effective amount of the formula I, particularly WT-51 and WT-52, as defined by the above formula Ia and Ib as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds of the formula I, particularly WT-51 and WT-52, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds of the formula I, particularly WT-51 and WT-52, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

EXAMPLES

The following Examples are illustrative and are not intended to limit the scope of the claimed subject matter.

For Example 1 and Example 2, ultraviolet (UV) absorption spectra were recorded with a Beckman-Coulter DU 530 UV/Vis spectrophotometer in the solvent noted. $^1$H nuclear magnetic resonance (NMR) spectra were recorded at 400 MHz or 500 MHz with Bruker Instruments DMX-400 and DMX-500 Avance console spectrometers in the solvent noted. $^{13}$C nuclear magnetic resonance (NMR) spectra were recorded at 101 MHz or 126 MHz with Bruker Instruments DMX-400 and DMX-500 Avance console spectrometers in the solvent noted. Chemical shifts (δ) are reported downfield from internal Me$_4$Si (δ 0.00). Electron impact (EI) mass spectra were recorded with Micromass AutoSpec (Beverly, Mass.) instrument. High-performance liquid chromatography (HPLC) was performed on a Waters Associates liquid chromatograph equipped with a Model Delta 600 solvent delivery system, a Model 600 Controller, a Rheodyne 7725i injector and a Model 2487 Dual λ Absorbance Detector. Optical rotary values were recorded with Perkin-Elmer Model 343 polarimeter at the concentration and in the solvent noted.

Example 1

Preparation of (22E)-(24R)-2-methylene-22-dehydro-1α,24,25-trihydroxy-19-nor-vitamin D$_3$ (Compound WT-51) and (22E)-(24S)-2-methylene-22-dehydro-1α,24,25-trihydroxy-19-nor-vitamin D$_3$ (Compound WT-52)

(22E)-Des-A,B-8β-benzoyloxy-24-oxo-25-[(triethylsilyl)oxy]-22-dehydrocholestan (3)

To a stirred solution of 2 (Scheme 1; 250 mg; 0.64 mmol) in tetrahydrofuran (1.5 ml) 1M solution of lithium hexamethyldisilazide in tetrahydrofuran (700 μl; 0.70 mmol) was added dropwise. After 1 h a solution of 1$^1$ (200 mg; 0.64 mmol) in tetrahydrofuran (1.5 ml) was added via cannula. The reaction mixture was stirred for 3 days. Then saturated aqueous solution of NH$_4$Cl (2 ml), brine (2 ml) and water (5 ml) was added at 0° C. and the resulting mixture was extracted with methylene dichloride (3×50 ml). Organic phase was dried over anhydrous Na$_2$SO$_4$, concentrated under reduced pressure and the residue was purified by column chromatography (2-5% ethyl acetate/hexane) to give 200 mg (0.39 mmol; 61% yield) of 3. [α]$_D$=+94.3 (c 1.1, CHCl$_3$), $^1$H NMR (400 MHz, CDCl$_3$) δ 0.60 (6H, q, J=7.9 Hz), 0.95 (9H, t, J=7.9 Hz), 1.10 (3H, s), 1.12 (3H, d, J=6.6 Hz), 1.34 (6H, s), 2.04 (2H, m) 2.32 (1H, m), 5.42 (1H, br d, J=1.9 Hz), 6.71 (1H, d, J=15.4 Hz), 6.84 (1H, dd, J=15.4 Hz, J=8.6 Hz), 7.45 (2H, t, J=7.4 Hz), 7.56 (1H, t, J=7.4 Hz), 8.05 (2H, d, J=7.4 Hz); $^{13}$C NMR (101 MHz, CDCl$_3$) δ 6.5, 7.0, 13.8, 18.0, 19.2, 22.6, 27.0, 27.1, 27.2, 30.5, 39.8, 42.2, 51.4, 55.4, 72.0, 78.8, 121.7, 128.4, 129.5, 132.7, 153.2, 166.4, 203.2; Exact mass (ESI) calculated for C$_{31}$H$_{49}$O$_4$Si ([M+H]$^+$) 513.3395. found 513.3405.

(22E)-Des-A,B-8β-benzoyloxy-24-hydroxy-25-(triethylsilyl)oxy-22-dehydrocholestan (4, mixture of 24-isomers)

To a stirred solution of 3 (200 mg; 0.39 mmol) in tetrahydrofuran (1.5 ml) and ethanol (4.5 ml) CeCl$_3$×7H$_2$O (298 mg; 0.80 mmol) and NaBH$_4$ (46 mg; 1.20 mmol) was added at 0° C. After 30 min. saturated aqueous solution of NH$_4$Cl (2 ml) and water (5 ml) were added and the mixture was extracted with methylene dichloride (3×40 ml). Organic phase was dried over anhydrous Na$_2$SO$_4$, concentrated under reduced pressure and the residue was purified by column chromatography (5-15% ethyl acetate/hexane) to give 180 mg (0.35 mmol; 90% yield) of 4 as a mixture of 24-diastereoisomers. Exact mass (ESI) calculated for C$_{31}$H$_{50}$O$_4$SiNa ([M+Na]$^+$) 537.3371. found 537.3380.

(22E)-Des-A,B-8β-benzoyloxy-24,25-di-[(triethylsilyl)oxy]-22-dehydrocholestan (5, mixture of 24-isomers)

To a stirred solution of 4 (150 mg; 0.29 mmol) and 2,6-lutidine (67 μl; 62 mg; 0.58 mmol) in methylene dichloride (1 ml) triethylsilyl trifluoromethanesulfonate (79 μl; 92 mg; 0.35 mmol) was added dropwise at −50° C. After 20 min. wet methylene dichloride (1 ml) and water (5 ml) was added and the mixture was extracted with methylene dichloride (3×25 ml). Organic phase was dried over anhydrous Na$_2$SO$_4$ and concentrated under reduced pressure. The residue was purified by column chromatography (hexane—3% ethyl acetate/hexane) to give 165 mg (0.26 mmol; 90% yield) of 5. Exact mass (ESI) calculated for C$_{37}$H$_{64}$O$_4$Si$_2$Na ([M+Na]$^+$) 651.4236. found 651.4234.

(22E)-Des-A,B-24,25-di-[(triethylsilyl)oxy]-22-dehydrocholestan-8β-ol (6, mixture of 24-isomers)

A solution of 5 (160 mg; 0.25 mmol) in tetrahydrofuran (3 ml) was treated with a 3M solution of methylmagnesium bromide in diethyl ether (750 μl; 2.25 mmol) for 5 h at 0° C. Saturated aqueous solution of NH$_4$Cl (2 ml), brine (2 ml) and water (5 ml) was carefully added and the mixture was extracted with methylene dichloride (3×25 ml). Organic phase was dried over anhydrous Na$_2$SO$_4$ and concentrated under reduced pressure. The residue was purified on a silica gel Sep-Pack cartridge (5-15% ethyl acetate/hexane) to give 106 mg (0.20 mmol; 81% yield) of 6. Exact mass (ESI) calculated for C$_{30}$H$_{60}$O$_3$Si$_2$Na ([M+Na]$^+$) 547.3974. found 547.3957.

(22E)-Des-A,B-24,25-di-[(triethylsilyl)oxy]-22-dehydrocholestan-8-one (7, mixture of 24-isomers)

A solution of 6 (65 mg; 120 μmol) and pyridinium p-toluenesulfonate (2 crystals) in methylene dichloride (6 ml) was treated with pyridinium dichromate (150 mg; 400 mmol) for 3 h. The mixture was purified on a silica gel Sep-Pack cartridge (3-7% ethyl acetate/hexane) to give 54 mg (103 μmol; 86%) of 7. Exact mass (ESI) calculated for C$_{30}$H$_{58}$O$_3$Si$_2$Na ([M+Na]$^+$) 545.3817. found 545.3817.

(22E)-(24R)-2-Methylene-22-dehydro-1α,24,25-trihydroxy-19-norvitamin $D_3$ (10, WT-51) and (22E)-(24S)-2-Methylene-22-dehydro-1α,24,25-trihydroxy-19-norvitamin $D_3$ (11, WT-52)

Figure 7:
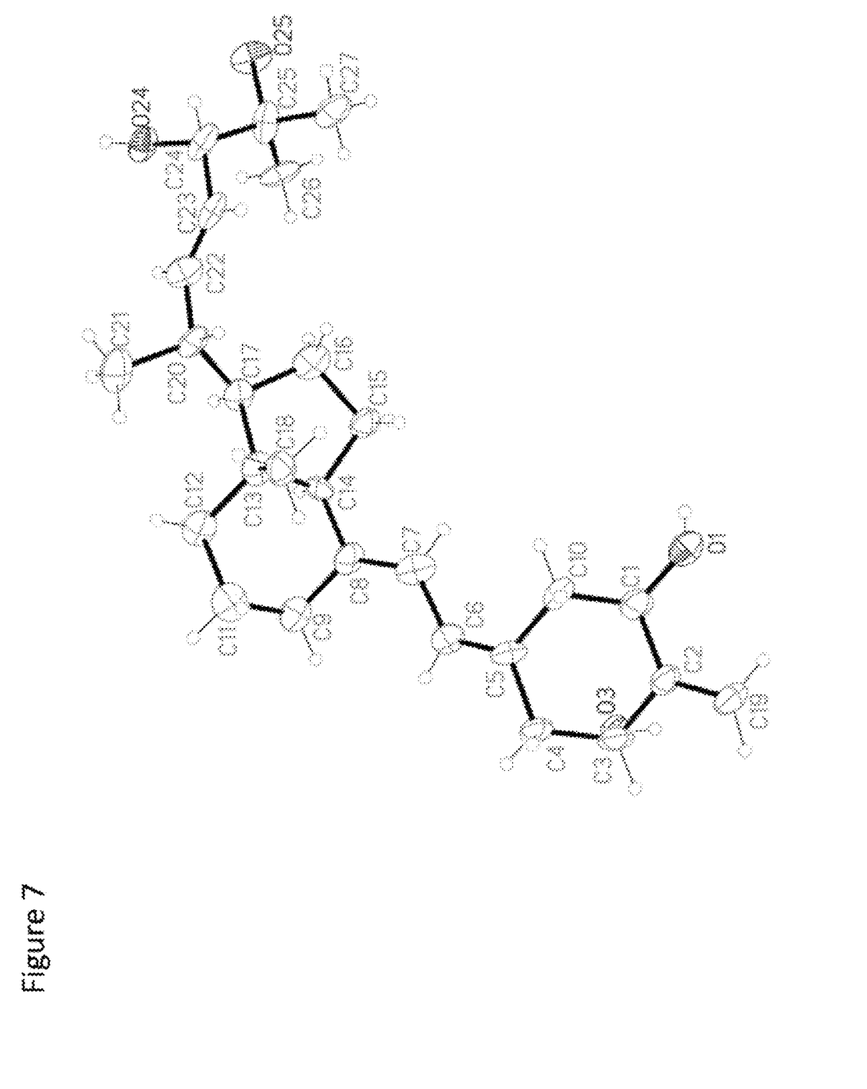
FIG. 7 illustrates an X-ray analysis of WT-52.

To a stirred solution of 8 (87 mg; 150 mmol) in tetrahydrofuran (1.5 ml) two drops of 1.8M phenyl lithium solution in di-n-butyl ether was added at −25° C. and the solution turned deep orange. Then stoichiometric amount of phenyl lithium solution (78 μl; 140 μmol) was added dropwise. After 20 min. the mixture was cooled to −78° C. and a solution of 7 (53 mg; 101 μmol) in tetrahydrofuran (0.75 ml) was transferred via cannula. The mixture was stirred for 2 h, warmed to 0° C. and stirred for next 2 h. Saturated aqueous solution of $NH_4Cl$ (1 ml), brine (1 ml) and water (5 ml) was carefully added and the mixture was extracted with hexane (3×25 ml). Organic phase was dried over $Na_2SO_4$ and concentrated under reduced pressure. The residue was purified on a silica gel Sep-Pack cartridge (hexane—2% ethyl acetate/hexane) to give 90 mg of crude 9. Crude 9 was dissolved in acetonitrile (2 ml) and treated with (±)-camphor-10-sulfonic acid (40 mg; 172 μmol) for 2 days. The mixture was purified on a previously treated with 10 drops of triethylamine silica gel Sep-Pack cartridge (10-30% 2-propanol/hexane) to give 28 mg (65 μmol; 64% yield from 7) of 10 and 11 as a mixture of diastereoisomers. The mixture was separated on HPLC (15% water/methanol; Zorbax-Eclipse XDB C18 5 μm; 3.5 ml/min.; $R_t$=5.30 min. for 10 and $R_t$=5.80 min. for 11) to give 9.5 mg (22 μmol; 22% yield from 7) of 10 and 13.5 mg (31 μmol; 31% yield from 7) of 11. X-ray analysis of 11 (FIG. 7) has shown 24S configuration. 10: UV (EtOH) $\lambda_{max}$=245, 252, 262 nm; $^1$H NMR (500 MHz, $CD_3OD$) δ 0.60 (3H, s), 1.07 (3H, d, J=6.6 Hz), 2×1.13 (3H each, s), 2.25-2.31 (2H, m), 2.48 (1H, dd, J=13.4 Hz, J=3.8 Hz), 2.66 (1H, dd, J=13.2 Hz, J=4.3 Hz), 2.85 (1H, dd, J=12.2 Hz, J=3.8 Hz), 3.73 (1H, d, J=7.4 Hz), 4.37 (1H, m), 4.41 (1H, m), 5.04 (1H, s), 5.05 (1H, s), 5.43 (1H, dd, J=15.4 Hz, J=7.5 Hz), 5.52 (1H, dd, J=15.4 Hz, J=8.6 Hz), 5.90 (1H, d, J=11.1 Hz), 6.26 (1H, d, J=11.1 Hz); 11: UV (EtOH) $\lambda_{max}$=244, 252, 261 nm; $^1$H NMR (500 MHz, $CD_3OD$) δ 0.60 (3H, s), 1.06 (3H, d, J=6.6 Hz), 1.12 (3H, s), 1.13 (3H, s), 1.65-1.70 (2H, m), 1.79-1.83 (1H, m), 1.93-2.07 (2H, m), 2.13 (1H, m), 2.25-2.31 (2H, m), 2.48 (1H, dd, J=13.3 Hz, J=3.9 Hz), 2.67 (1H, dd, J=13.2 Hz, J=4.3 Hz), 2.85 (1H, dd, J=12.2 Hz, J=3.7 Hz), 3.75 (1H, d. J=6.7 Hz), 4.37 (1H, m), 4.41 (1H, m), 5.04 (1H, s), 5.06 (1H, s), 5.45 (1H, dd, J=15.4 Hz, J=6.9 Hz), 5.57 (1H, dd, J=15.4 Hz, J=8.4 Hz), 5.90 (1H, d, J=11.1 Hz), 6.26 (1H, d, J=11.1 Hz); MS (EI) m/1430 (M⁺, 10), 396 (7), 253 (22), 91 (100); exact mass (ESI) calculated for $C_{27}H_{42}O_4Na$ ([M+Na]⁺) 453.2976. found 453.2977.

Scheme I.

3

7

8

9. $R^1$ = TES; $R^2$ = TBS

10. WT-51 24R; $R^1$ = $R^2$ = H;

11. WT-52 24S; $R^1$ = $R^2$ = H (i) LiHMDS, THF, 61%; (ii) NaBH$_4$, CeCl$_3$x7 H$_2$O, EtOH, THF, 90%; (iii) TESOTf, 2, 6-lutidine, CH$_2$Cl$_2$, 90%; (iv) MeMgBr, Et$_2$O, THF, 81%; (v) PDC, PPTS, CH$_2$Cl$_2$, 86%; (vi) PhLi, (n-Bu)$_2$O, THF; (vii) CSA, MeCN, 22% of 10 from 7 and 31% of 11 from 7.

Example 2

Preparation of 1-(Dimetoxyphosphoryl)-3-methyl-3-[(triethylsilyl)oxy]-2-butanone (Compound 2)

3-Methyl-3-[(triethylsilyl)oxy]-2-butanone (13)

To a stirred solution of 3-hydroxy-3-methyl-2-butanone (Scheme 2; 1.20 ml; 1.16 g; 11.4 mmol) and 2,6-lutidine (1.86 ml; 1.71 g; 16.0 mmol) in methylene dichloride (30 ml) triethylsilyl trifluoromethanesulfonate (3.11 ml; 3.61 g; 13.7 mmol) was added dropwise at −50° C. After 20 min. wet methylene dichloride (5 ml) and water (50 ml) was added and the mixture was extracted with methylene dichloride (3×100 ml). Organic phase was dried over anhydrous Na$_2$SO$_4$ and concentrated under reduced pressure. The residue was purified by column chromatography (hexane—3% ethyl acetate/hexane) to give 2.40 g (10.4 mmol; 91% yield) of 13. $^1$H NMR (500 MHz, CDCl$_3$) δ 0.63 (6H, q, J=7.9 Hz), 0.97 (9H, t, J=7.9 Hz), 1.33 (6H, s), 2.23 (3H, s); $^{13}$C NMR (126 MHz, CDCl$_3$) δ 6.5, 7.0, 27.0, 27.7, 79.7, 214.0; MS (EI) m/z 216 ([M−Et]$^+$, 100), 173 (81), 172 (30) 115 (68), 87 (67); exact mass calculated for C$_9$H$_{19}$O$_2$Si ([M−Et]$^+$) 187.1149. found 187.1144.

1-Bromo-3-methyl-3-[(triethylsilyl)oxy]-2-butanone (14)

To a stirred solution of 13 (2.40 g; 10.4 mmol) and triethylamine (2.92 ml; 2.12 g; 21.0 mmol) in methylene dichloride (50 ml) triethylsilyl trifluoromethanesulfonate (2.37 ml; 2.75 g; 10.4 mmol) was added dropwise at 0° C. After 15 min. N-bromosuccinimide (2.05 g; 11.5 mmol) was added and a cooling bath was removed. After 30 min. saturated aqueous solution of NH$_4$Cl (10 ml) and water (50 ml) was added and the mixture was extracted with methylene dichloride (3×100 ml). Organic phase was dried over anhydrous Na$_2$SO$_4$ and concentrated under reduced pressure. The residue was purified by column chromatography (hexane—5% ethyl acetate/hexane) to give 1.55 g (5.25 mmol; 50% yield) of 14. $^1$H NMR (400 MHz, CDCl$_3$) δ 0.64 (6H, q, J=7.9 Hz), 0.97 (9H, t, J=7.9 Hz), 1.41 (6H, s), 4.44 (2H, s); $^{13}$C NMR (101 MHz, CDCl$_3$) δ 6.5, 7.0, 27.8, 33.6, 80.4, 206.2; MS (EI) m/z 294 and 296 ([M−Et]$^+$, 24 and 23), 187 (45), 173 (100); exact mass calculated for C$_9$H$_{18}$O$_2$BrSi ([M−Et]$^+$) 265.0254. found 265.0247.

1-(Dimetoxyphosphoryl)-3-methyl-3-[(triethylsilyl)oxy]-2-butanone (2)

A solution of 14 (1.55 g; 5.25 mmol) and trimethyl phosphite (514 μl; 782 mg; 6.31 mmol) in toluene (20 ml) was refluxed for 3 days. The mixture was purified by column chromatography (5-15% 2-propanol/hexane) to give 1.54 g (4.75 mmol; 90% yield) of 2. $^1$H NMR (400 MHz, CDCl$_3$) δ 0.65 (6H, q, J=7.9 Hz), 0.98 (9H, t, J=7.9 Hz), 1.36 (6H, s), 3.40 (2H, d, J$_{H-P}$=20.7 Hz) 3.80 (6H, d, J$_{H-P}$=11.2 Hz); $^{13}$C NMR (101 MHz, CDCl$_3$) δ 6.4, 6.9, 26.8, 33.7 (d, J$_{C-P}$=137.8 Hz), 52.8 (d, J$_{C-P}$=6.7 Hz) 80.0, 207.1 (d, J$_{C-P}$=6.0 Hz); MS (EI) m/z 324 ([M−Et]$^+$, 98), 238 (65), 211 (61), 173 (100); exact mass calculated for C$_{11}$H$_{24}$O$_5$PSi ([M−Et]$^+$) 295.1126. found 295.1126.

Scheme II.

(i) TESOTf, 2,6-lutidine, CH$_2$Cl$_2$, 91%; (ii) TESOTf, Et$_3$N, CH$_2$Cl$_2$; NBS, 50%; (iii) P(OME)$_3$, PhMe, 90%.

Example 3

Biological Activity of (22E)-(24R)-2-methylene-22-dehydro-1α,24,25-trihydroxy-19-nor-vitamin DD (Compound WT-51) and (22E-(24S)-2-methylene-22-dehydro-1α,24,25-trihydroxy-19-nor-vitamin D$_3$ (Compound WT-52)

Experimental Methods

Vitamin D Receptor Binding
Protein Source.

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs.

Unlabeled ligands were dissolved in ethanol and the concentrations determined using UV spectrophotometry (1,25 (OH)$_2$D$_3$: molar extinction coefficient=18,200 and 1$_{max}$=265 nm; Analogs: molar extinction coefficient=42,000 and 1$_{max}$=252 nm). Radiolabeled ligand ($^3$H-1,25(OH)$_2$D$_3$, ~159 Ci/mmole) was added in ethanol at a final concentration of 1 nM.

Assay Conditions.

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxyapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Study Drugs.

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells.

Human promyelocytic leukemia (HL-60) cells were grown in RPMI-1640 medium containing 10% fetal bovine serum. The cells were incubated at 37° C. in the presence of 5% CO$_2$.

Assay Conditions.

HL-60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24OHase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive intraperitoneal doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Bone Nodule Assay

A human osteoblast cell line was purchased from ATCC (CRL-1372). These cells were grown at 34 C with 5% CO$_2$ in DMEM-F12, 10% FBS. Four to five days after plating cells (2-4×10$^4$ cells/well) in a 12-well plate, drug administration began. Two vitamin D analogs were tested, WT-51 and 2MD. (See DeLuca et al., U.S. Pat. No. 5,843,928). The tested doses included concentrations of 10$^{-8}$M, 10$^{-9}$M, 10$^{-10}$M, 10$^{-11}$M, 10$^{-12}$M, or 10$^{-13}$M. Three separate doses were administered separated by ~48 hours between dosings. Two days after the last vehicle (ethanol at <1% v/v) or vitamin D analog dose was administered, the cells were incubated in ascorbic acid and b-glycerol phosphate for six days. The cells were then stained with silver nitrate to reveal the mineralized bone nodules.

Ovariectomized Rat Model

Virgin Sprague-Dawley female rats were either sham-operated or ovariectomized (OVX) at 4 months of age by the vendor (Harlan). Starting at 16 weeks post-surgery, the animals were given vehicle or test analog (WT or 2MD) once daily for 17 weeks. Bone mineral density (BMD) and serum and urinary calcium levels were assessed periodically throughout the study. At termination, femurs were collected for bone strength testing (3-point bending, Numira Biosciences).

Interpretation of the Biological Activity Data

Figure 1:
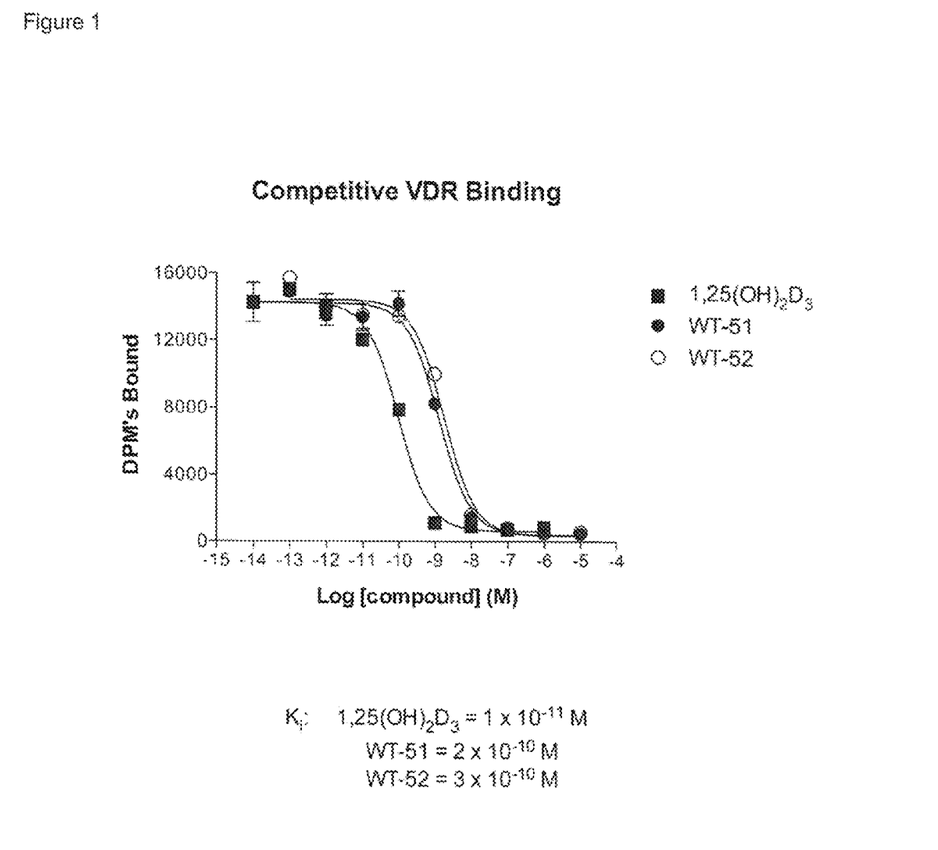
FIG. 1 illustrates competitive binding to the nuclear hormone receptor by the disclosed compounds and the native hormone (i.e., $1,25(OH)_2D_3$). As illustrated, WT-51 and WT-52 compete for binding to the VDR ~one log less than the native hormone.
Figure 2:
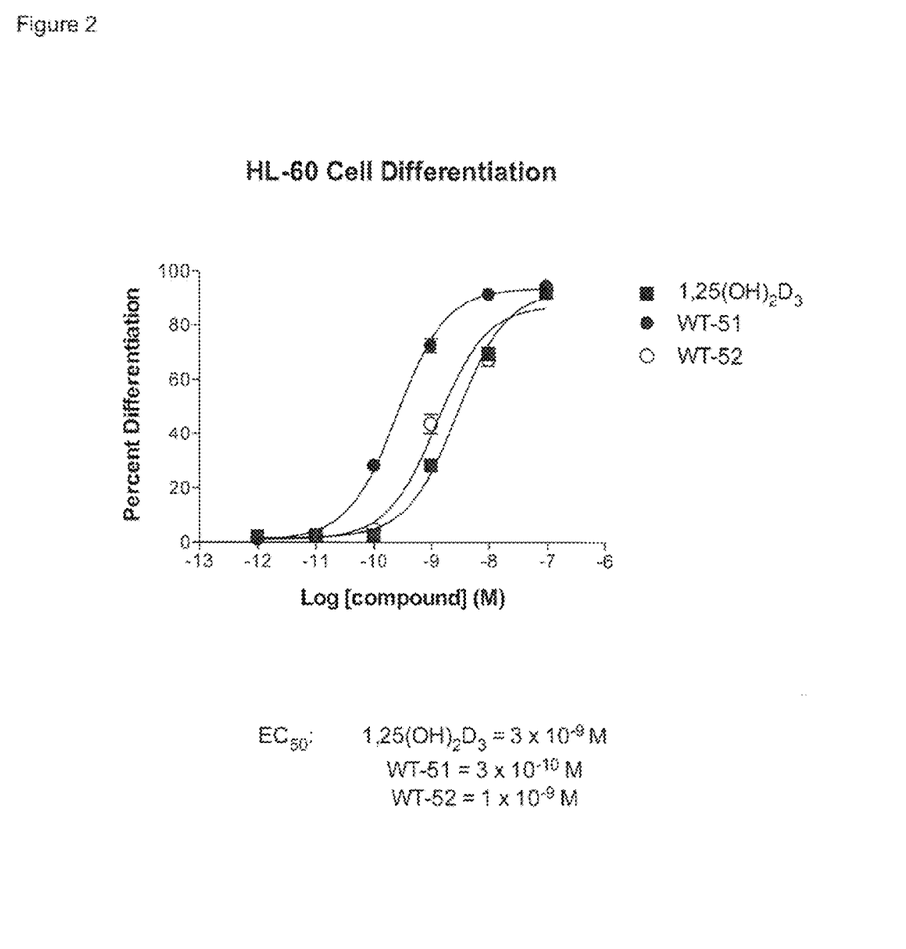
FIG. 2 illustrates induction of HL-60 cell differentiation by the disclosed compounds and the native hormone. As illustrated, WT-51 is approximately 10× more potent than the native hormone in promoting cell differentiation, whereas WT-52 is similar in potency to the native hormone.
Figure 3:
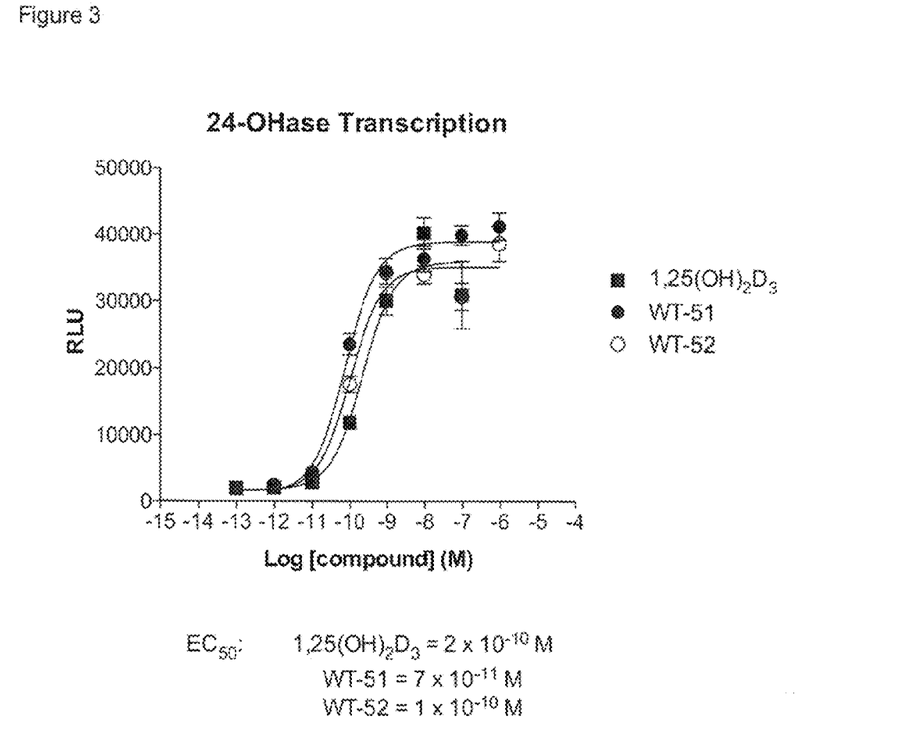
FIG. 3 illustrates induction of in vitro transcription by the disclosed compounds and the native hormone. As illustrated, WT-51 is nearly one log more potent than the native hormone in stimulation of gene transcription, whereas WT-52 has approximately the same activity as the native hormone.

As illustrated in FIG. 1, compounds WT-51 and WT-52 were approximately 10× less active at binding to the vitamin D receptor (VDR) as compared to the natural hormone. However, as illustrated in FIG. 2, compound WT-51 was approximately 10× more effective than the natural hormone at promoting cell differentiation of HL-60 cells. Furthermore, as illustrated in FIG. 3, compound WT-51 was approximately 10× more effective than the natural hormone at stimulating gene transcription from the 24OHase gene promoter. These results suggest that the analogs disclosed herein will be effective for treating diseases such as psoriasis because the analogs, and WT-51 in particular, have direct cellular activity in causing differentiation and in suppressing growth. These results also suggest that the presently disclosed analogs, and WT-51 in particular, will be effect as anti-cancer agents, especially against leukemia, neuroblastoma, retinoblastoma, melanoma, colon cancer, breast cancer and prostate cancer.

Figure 4:
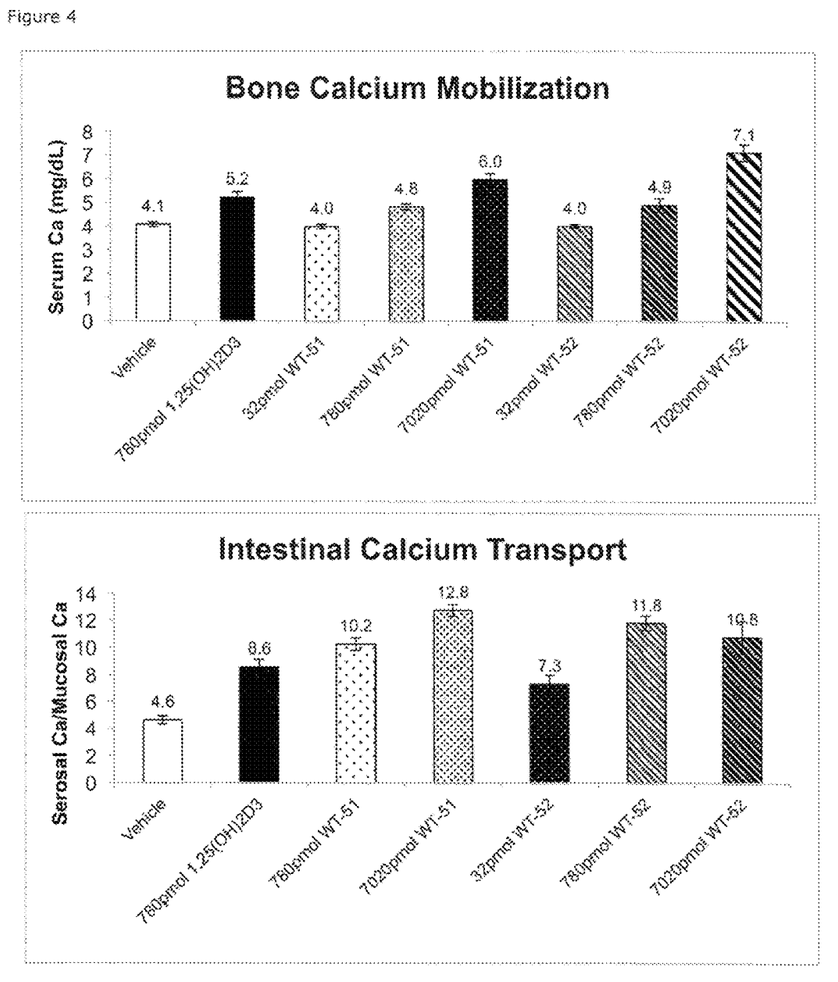
FIG. 4 illustrates calcium mobilization and intestinal calcium transport in the rat by the disclosed compounds and the native hormone. In both bone and intestine, WT-51 and WT-52 display similar potency to the native hormone

As illustrated in FIG. 4, compounds WT-51 and WT-52 display similar potency as the native hormone with respect to bone calcium mobilization and intestinal calcium transport. This suggests that compounds WT-51 and WT-52 will not present an increased risk for hypercalcemia when utilized as therapeutic agents as compared to the native hormone.

Figure 5:
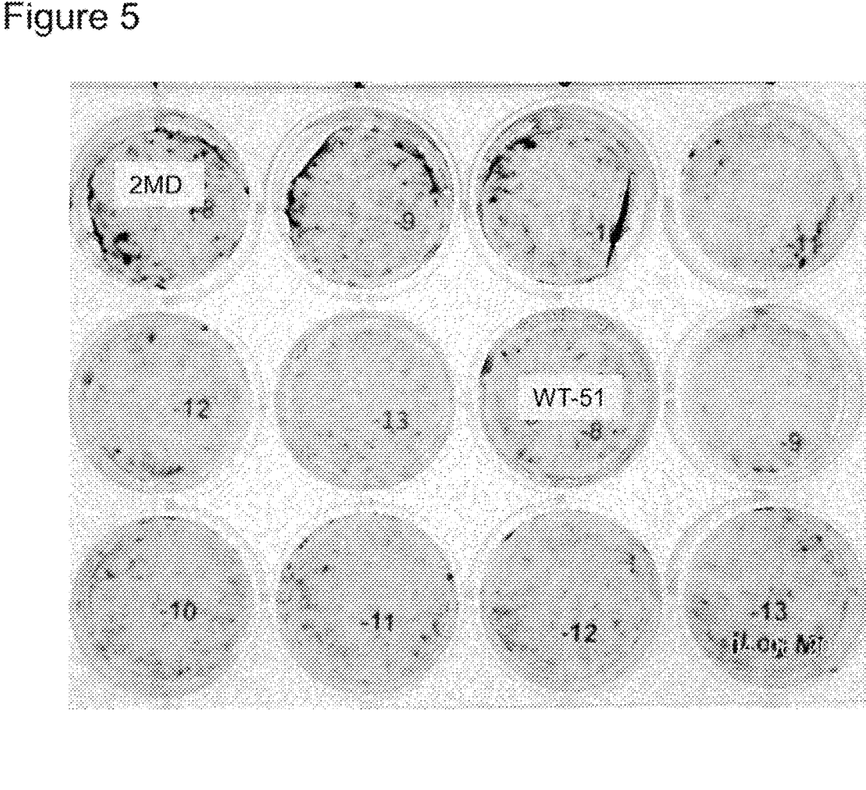
FIG. 5 illustrates bone nodule induction by WT-51 and 2-methylene-(20S)-1α,25-dihydroxy-19-nor vitamin $D_3$, otherwise referred to as "2MD." As illustrated, WT-51 exhibits similar potency to 2MD in bone nodule induction.
Figure 6:
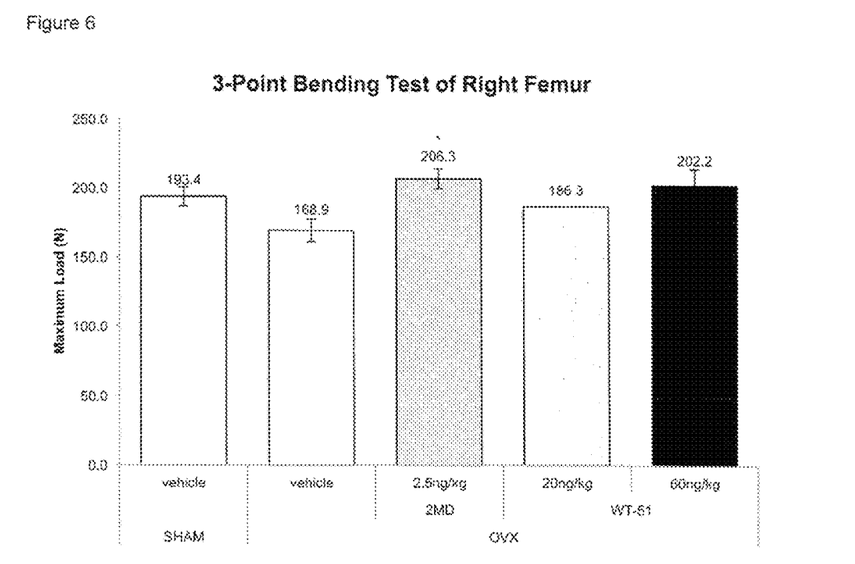
FIG. 6 illustrates bone strength testing after treatment with WT-51 or 2MD. A illustrated, WT-51 at a concentration of 60 ng/kg body weight improves bone strength in ovariectomized rats to the same degree as 2MD at 2.5 ng/kg body weight.

As illustrated in FIG. 5, compound WT-51 displayed similar potency as compound 2MD with respect to nodule formation. As illustrated in FIG. 6, WT-51 at a concentration of 60 ng/kg body weight improved bone strength in ovariectomized rats to the same degree as 2MD at a concentration of 2.5 ng/kg body weight. Because of the strong potency of WT-51 in stimulating bone formation and increasing bone strength without correspondingly increasing intestinal calcium transport or bone calcium mobilation, WT-51 may serve as an important therapy for the prevention and treatment of various bone disorders including osteoporosis and bone metabolic disorders.

Conclusion of Biological Findings

Desaturation of the 22-carbon and introduction of a 24-hydroxyl results in compounds that bind to the vitamin D receptor (VDR) with one log lower affinity than the natural hormone regardless of the orientation of the 24-hydroxyl group. Cell differentiation and in vitro transcription, on the other hand, are significantly affected by the orientation of the 24-hydroxyl group with the analog in the R configuration (WT-51) exhibiting one log higher potency than the analog in the S configuration (WT-52) or the natural hormone. The enhanced potency of WT-51 is also observed in an in vitro model of bone formation where WT-51 exhibits potency similar to 2MD. Additional testing of WT-51 in a rat model of osteopenia shows it can increase bone strength similar to 2MD. In vivo, both WT-51 and WT-52 show similar intestinal calcium transport and bone resorption activity as compared to the native hormone. Because of the strong potency of WT-51 in stimulating bone formation and increasing bone strength without a corresponding increase in intestinal calcium transport or bone calcium mobilization, WT-51 may serve as an important therapy for the prevention and treatment of various bone disorders and diseases.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound of the formula:

where $X_1$, $X_2$, $X_3$, and $X_4$, which are the same or different, are each selected from hydrogen or a hydroxy-protecting group.
2. The compound of claim 1, wherein $X_1$ and $X_2$ are t-butyldimethylsilyl.
3. The compound of claim 1, wherein $X_1$ and $X_2$ are hydrogen.
4. The compound of claim 1, wherein $X_3$ and $X_4$ are triethylsilyl.
5. The compound of claim 1, wherein $X_3$ and $X_4$ are hydrogen.
6. The compound of claim 1, wherein $X_1$, $X_2$, $X_3$, and $X_4$ are hydrogen.
7. A compound of the formula:

and named (22E)-(24R)-2-methylene-22-dehydro-1α,24,25-trihydroxy-19-nor-vitamin $D_3$.
8. A compound of the formula:

and named (22E)-(24S)-2-methylene-22-dehydro-1α,24,25-trihydroxy-19-nor-vitamin $D_3$.
9. A pharmaceutical composition containing an effective amount of the compound of claim 7 and a pharmaceutically acceptable excipient.
10. A pharmaceutical composition containing an effective amount of the compound of claim 8 and a pharmaceutically acceptable excipient.
11. A method of treating osteoporosis in a patient in need thereof, the method comprising administering to the patient an effective amount of the compound of claim 7.
12. A method of treating osteoporosis in a patient in need thereof, the method comprising administering to the patient an effective amount of the compound of claim 8.

13. A method for increasing bone strength in a patient in need thereof, the method comprising administering to the patient an effective amount of the compound of claim 7.

14. A method for increasing bone strength in a patient in need thereof, the method comprising administering to the patient an effective amount of the compound of claim 8.

15. A method of treating leukemia in a patient in need thereof, the method comprising administering to the patient an effective amount of the compound of claim 7.

16. A method of treating leukemia in a patient in need thereof, the method comprising administering to the patient an effective amount of the compound of claim 8.

17. A method of treating secondary hyperparathyroidism of renal osteodystrophy in a patient in need thereof, the method comprising administering to the patient an effective amount of the compound of claim 7.

18. A method of treating secondary hyperparathyroidism of renal osteodystrophy in a patient in need thereof, the method comprising administering to the patient an effective amount of the compound of claim 8.

* * * * *